US012396974B2

(12) United States Patent
Llosa

(10) Patent No.: US 12,396,974 B2
(45) Date of Patent: Aug. 26, 2025

(54) KETONE ESTER AS A THERAPEUTIC TREATMENT OF COVID-19 AND RELATED VIRAL INFECTIONS

(71) Applicant: KETONEAID, INC., Falls Church, VA (US)

(72) Inventor: Frank Borges Llosa, Fall Church, VA (US)

(73) Assignee: KetoneAid, Falls Church, VA (US)

( * ) Notice: Subject to any disclaimer, the term of this patent is extended or adjusted under 35 U.S.C. 154(b) by 540 days.

(21) Appl. No.: 17/907,470

(22) PCT Filed: Mar. 26, 2021

(86) PCT No.: PCT/US2021/024323
§ 371 (c)(1),
(2) Date: Sep. 27, 2022

(87) PCT Pub. No.: WO2021/195477
PCT Pub. Date: Sep. 30, 2021

(65) Prior Publication Data
US 2023/0119628 A1  Apr. 20, 2023

Related U.S. Application Data

(60) Provisional application No. 63/001,000, filed on Mar. 27, 2020.

(51) Int. Cl.
| | |
|---|---|
| *A61K 31/22* | (2006.01) |
| *A61K 31/047* | (2006.01) |
| *A61K 31/19* | (2006.01) |
| *A61K 31/23* | (2006.01) |
| *A61K 31/375* | (2006.01) |
| *A61K 31/706* | (2006.01) |
| *A61P 31/14* | (2006.01) |

(52) U.S. Cl.
CPC ............ *A61K 31/22* (2013.01); *A61K 31/047* (2013.01); *A61K 31/19* (2013.01); *A61K 31/23* (2013.01); *A61K 31/375* (2013.01); *A61K 31/706* (2013.01); *A61P 31/14* (2018.01)

(58) Field of Classification Search
CPC combination set(s) only.
See application file for complete search history.

(56) References Cited

U.S. PATENT DOCUMENTS

| | | |
|---|---|---|
| 4,997,976 A | 3/1991 | Brunengraber et al. |
| 5,112,865 A | 5/1992 | Nichels et al. |
| 5,126,373 A | 6/1992 | Brunengraber et al. |
| 6,207,856 B1 | 3/2001 | Veech |
| 6,316,038 B1 | 11/2001 | Veech |
| 6,323,237 B1 | 11/2001 | Veech |
| 6,380,244 B2 | 4/2002 | Martin et al. |
| 6,613,356 B1 | 9/2003 | Vlahakos |
| 7,351,736 B2 | 4/2008 | Veech |
| 8,101,653 B2 | 1/2012 | Veech |
| 8,642,654 B2 | 2/2014 | Clarke et al. |
| 9,034,613 B2 | 5/2015 | Robertson et al. |
| 9,138,420 B2 | 9/2015 | D'Agostino et al. |
| 9,211,275 B2 | 12/2015 | Clarke et al. |
| 9,579,302 B2 | 2/2017 | Veech et al. |
| 10,051,880 B2 | 8/2018 | Clarke et al. |
| 10,154,982 B2 | 12/2018 | Clarke et al. |
| 10,245,242 B1 | 4/2019 | Millet |
| 10,292,952 B2 | 5/2019 | Millet |
| 10,376,482 B2 | 8/2019 | Cavaleri |
| 10,478,415 B2 | 11/2019 | Veech et al. |
| 10,588,876 B2 | 3/2020 | Millet |
| 10,596,129 B2 | 3/2020 | Millet |
| 10,596,313 B2 | 3/2020 | Gregory et al. |
| 10,736,861 B2 | 8/2020 | Millet |
| 11,033,553 B2 | 6/2021 | Millet |
| 11,044,932 B1 | 6/2021 | Price et al. |
| 11,173,138 B2 | 11/2021 | Lowery et al. |
| 2003/0138384 A1 | 7/2003 | Stephenson et al. |
| 2006/0280721 A1 | 12/2006 | Veech et al. |
| 2010/0004194 A1 | 1/2010 | Berg et al. |
| 2011/0237666 A1 | 9/2011 | Clarke et al. |
| 2011/0287131 A1 | 11/2011 | Murali et al. |
| 2012/0329742 A1 | 12/2012 | Weg |
| 2014/0010939 A1 | 1/2014 | Krohn et al. |
| 2014/0308719 A1 | 10/2014 | Clarke et al. |

(Continued)

FOREIGN PATENT DOCUMENTS

| | | |
|---|---|---|
| AU | 2004245567 A1 | 12/2004 |
| EP | 1755743 A2 | 2/2007 |

(Continued)

OTHER PUBLICATIONS

Challener, C., "Bio-butylene Glycol Makes Its Debut," ICIS Chemical Business, 13-19, p. 11, ICIS, New York, United States (Oct. 2017).

Kashiwaya, Y., et al., "A Ketone Ester Diet Increases Brain Malonyl-coa and Uncoupling Proteins 4 and 5 While Decreasing Food Intake in the Normal Wistar Rat," The Journal of Biological Chemistry 285(34):25950-25956, ASBMB, United States (Jun. 2010).

Office Action mailed Mar. 11, 2025, in United States U.S. Appl. No. 18/364,136, LLosa, F.B., et al., filed Aug. 2, 2023, 30 pages.

Notice of Allowance mailed Apr. 1, 2024 in U.S. Appl. No. 18/350,563, Llosa, F., et al., filed Jul. 11, 2023, 8 pages.

(Continued)

*Primary Examiner* — Umamaheswari Ramachandran
(74) *Attorney, Agent, or Firm* — Sterne, Kessler, Goldstein & Fox P.L.L.C.

(57) ABSTRACT

Ketone bodies can be used to treat the human body from viral infections, and will overcome the cytokine storm, which leads to acute lung injury/acute respiratory distress syndrome. Based on this discovery, methods of treating humans from a viral infection like Covid-19 are disclosed which includes a therapeutically effective amount of an exogenous ketones including, but not limited to, ketone monoester (R)-3-hydroxybutyl (R)-3-hydroxybutanoate.

19 Claims, No Drawings

(56) References Cited

U.S. PATENT DOCUMENTS

| | | |
|---|---|---|
| 2014/0350105 A1 | 11/2014 | D'Agostino et al. |
| 2015/0065571 A1 | 3/2015 | Clarke et al. |
| 2015/0238494 A1 | 8/2015 | Owoc |
| 2016/0030314 A1 | 2/2016 | Clarke et al. |
| 2017/0266148 A1 | 9/2017 | D'Agostino et al. |
| 2017/0296501 A1 | 10/2017 | Lowery et al. |
| 2018/0057846 A1 | 3/2018 | Llosa et al. |
| 2018/0195096 A1 | 7/2018 | Veech et al. |
| 2019/0014798 A1 | 1/2019 | Clarke et al. |
| 2019/0119705 A1 | 4/2019 | Llosa et al. |
| 2019/0177673 A1 | 6/2019 | Llosa et al. |
| 2019/0201366 A1 | 7/2019 | Clarke et al. |
| 2020/0077690 A1 | 3/2020 | Steinberg |
| 2020/0121623 A1 | 4/2020 | Millet |
| 2020/0289444 A1 | 9/2020 | Thomas et al. |
| 2020/0347413 A1 | 11/2020 | Llosa et al. |
| 2020/0360517 A1 | 11/2020 | Clarke |
| 2020/0385331 A1 | 12/2020 | Llosa |
| 2021/0101855 A1 | 4/2021 | Khandurina et al. |
| 2024/0043778 A1 | 2/2024 | Llosa et al. |
| 2024/0067995 A1 | 2/2024 | Llosa |
| 2024/0074459 A1 | 3/2024 | Llosa |
| 2024/0301332 A1 | 9/2024 | Llosa et al. |
| 2024/0376503 A1 | 11/2024 | Llosa |
| 2025/0011695 A1 | 1/2025 | Llosa et al. |
| 2025/0011696 A1 | 1/2025 | Llosa et al. |

FOREIGN PATENT DOCUMENTS

| | | |
|---|---|---|
| WO | WO-199841201 A1 | 9/1998 |
| WO | WO-2005023290 A2 | 3/2005 |
| WO | WO-2006014353 A2 | 2/2006 |
| WO | WO-2010021766 A1 | 2/2010 |
| WO | WO-2010084356 A1 | 7/2010 |
| WO | WO-2013150153 A1 | 10/2013 |
| WO | WO-2014153416 A1 | 9/2014 |
| WO | WO-2014190251 A1 | 11/2014 |
| WO | WO-2015184279 A1 | 12/2015 |
| WO | WO-2017156446 A1 | 9/2017 |
| WO | WO-2018115158 A1 | 6/2018 |
| WO | WO-2019104082 A1 | 5/2019 |
| WO | WO-2019147503 A1 | 8/2019 |
| WO | WO-2019234402 A1 | 12/2019 |

OTHER PUBLICATIONS

Notice of Allowance mailed Aug. 10, 2023 in U.S. Appl. No. 16/168,703, Llosa, F.B., et al., filed Oct. 23, 2018, 7 pages.

Notice of Allowance mailed Aug. 7, 2024 in U.S. Appl. No. 18/298,851, Llosa, F., et al., filed Apr. 11, 2023, 7 pages.

Notice of Allowance mailed Jun. 12, 2023 in U.S. Appl. No. 16/168,703, Llosa, F., et al., filed Oct. 23, 2018, 7 pages.

Notice of Allowance mailed Jun. 3, 2024, 2024 in U.S. Appl. No. 18/350,563, Llosa, F., et al., filed Jul. 11, 2023, 8 pages.

Notice of Allowance mailed Mar. 14, 2024 in U.S. Appl. No. 18/298,851, Llosa, F., et al., filed Apr. 11, 2023, 7 pages.

Notice of Allowance mailed May 16, 2024 in U.S. Appl. No. 18/350,563, Llosa, F., et al., filed Jul. 11, 2023, 8 pages.

Office Action mailed Dec. 7, 2023, in U.S. Appl. No. 18/298,851, LLosa, F.B., et al., filed Apr. 11, 2023, 8 pages.

Office Action mailed Feb. 14, 2024, in U.S. Appl. No. 18/350,563, LLosa, F.B., et al., filed Jul. 11, 2023, 10 pages.

Prins, P.J., et al., "Dose Response of a Novel Exogenous Ketone Supplement on Physiological, Perceptual and Performance Parameters," Nutrition & Metabolism 17:81, pp. 1-12, BioMed Central, United Kingdom (Sep. 2020).

World Health Organization, "Butane-1,3-diol," International Programme of Chemical Safety: Toxicological Evaluation of Certain Food Additives, WHO Food Additives Series 14, Geneva (Apr. 2-11, 1979), 9 pages.

Advisory Committee on Novel Foods and Proccesses (ACNFP), "Application for the Approval of (3)-R-hydroxybutyl (3)-R-hydroxybutyrate Under Regulation (EC) No. 258/97 of the European Parliament and of the Council of Jan. 27, 1997 Concerning Novel Foods and Novel Food Ingredients," Government of the United Kingdom, United Kingdom, 69 pages (Jul. 24, 2013).

Barr, D., "The Myth Of Waxy Maize Starch And The Truth Behind It All!," bodybuilding.com, accessed at URL:[https://www.bodybuilding.com/fun/waxy_maize_starch_myth.htm] on Dec. 8, 2021, 6 pages (Jan. 2019).

Beneo-Institute, "Slow release carbohydrate," isomaltulose.org, accessed at URL:[https://isomaltulose.org/home/slow-release-carb/] on Dec. 7, 2021, BENEO GmbH, Germany, 1 page.

Burnett, A.L., "The Role of Nitric Oxide in Erectile Dysfunction: Implications for Medical Therapy," The Journal of Clinical Hypertension 8(s12):53-62, Wiley-Blackwell Publishing Ltd., United States (2006).

Clarke, K., et al., "Kinetics, safety and tolerability of (R)-3-hydroxybutyl (R)-3-hydroxybutyrate in healthy adult subjects," Regulatory Toxicology and Pharmacology 63(3), 19 pages, Elsevier, Netherlands (Aug. 2012).

Cox, P.J., et al., "Nutritional Ketosis Alters Fuel Preference and Thereby Endurance Performance in Athletes," Clinical and Translational Report 24(2):256-268, Elsevier Inc., Netherlands (2016).

Desrochers, S., et al., "R,S-1,3-butanediol acetoacetate esters, potential alternates to lipid emulsions for total parenteral nutrition," The Journal of Nutritional Biochemistry 6(2):111-118, Elsevier Inc., Netherlands (1995).

EndurElite, "Cluster Dextrin—The King Of Carbs For Endurance Athletes," endurlite.com, accessed at URL:[https://endurelite.com/blogs/free-nutrition-supplement-and-training-articles-for-runners-and-cyclists/king-of-carbs] on Dec. 8, 2021, 6 pages (Jun. 2018).

Le Sann, C., et al., "Assembly intermediates in polyketide biosynthesis: enantioselective syntheses of beta-hydroxycarbonyl compounds," Org Biomol Chem 3(9):1719-1728, Royal Society of Chemistry, United Kingdom (2005).

Maresch, C. C., et al., "Low Glycemic Index Prototype Isomaltulose—Update of Clinical Trials," Nutrients 9(4):381, 12 pages, MDPI, Switzerland (Apr. 2017).

Office Action mailed Mar. 22, 2019, in U.S. Appl. No. 15/688,690, Llosa, F.B., et al., filed Aug. 28, 2017, 9 pages.

Office Action mailed Jul. 11, 2022, in U.S. Appl. No. 16/947,036, Llosa, F.B., filed Jul. 15, 2020, 8 pages.

Office Action mailed Sep. 10, 2021, in U.S. Appl. No. 16/168,703, Llosa, F.B., filed Oct. 23, 2018, 9 pages.

Office Action mailed Apr. 28, 2022, in U.S. Appl. No. 16/168,703, Llosa, F.B., et al., filed Oct. 23, 2018, 8 pages.

Office Action mailed Dec. 20, 2022, in U.S. Appl. No. 16/168,703, Llosa, F.B., et al., filed Oct. 23, 2018, 16 pages.

Office Action mailed Jun. 16, 2020, in U.S. Appl. No. 16/167,449, Llosa, F.B., et al., filed Oct. 22, 2018, 11 pages.

Office Action mailed Feb. 22, 2021, in U.S. Appl. No. 16/167,449, Llosa, F.B., et al., filed Oct. 22, 2018, 12 pages.

Office Action mailed Aug. 31, 2021, in U.S. Appl. No. 16/167,449, Llosa, F.B., filed Oct. 22, 2018, 17 pages.

Office Action mailed Jul. 8, 2019, in U.S. Appl. No. 16/408,424, Llosa, F.B., filed May 9, 2019, 18 pages.

Office Action mailed Apr. 15, 2021, in U.S. Appl. No. 16/736,136, Llosa, F.B., filed Jan. 7, 2020, 20 pages.

Office Action mailed Feb. 2, 2022, in U.S. Appl. No. 17/455,826, Llosa, F.B., filed Nov. 19, 2021, 24 pages.

Office Action mailed Jul. 1, 2022, in U.S. Appl. No. 17/455,826, Llosa, F.B., filed Nov. 19, 2021, 19 pages.

Office Action mailed Feb. 21, 2023, in U.S. Appl. No. 17/455,826, Llosa, F.B., filed Nov. 19, 2021, 24 pages.

Notice of Allowance mailed Mar. 20, 2023, in U.S. Appl. No. 16/947,036, Llosa, F.B., filed Jul. 15, 2020, 4 pages.

KETONE ESTER AS A THERAPEUTIC TREATMENT OF COVID-19 AND RELATED VIRAL INFECTIONS

FIELD OF THE DISCLOSURE

The present disclosure relates to ketogenic compounds and compositions comprising ketogenic compounds capable of reducing adverse effects caused by or associated with a viral infection, such as the adverse effects caused by or associated with Covid-19 infection caused by the SARS-CoV-2 virus. The present disclosure also provides methods of using such ketogenic compounds and compositions comprising such ketogenic compounds to treat, reduce, ameliorate, or block one the cytokine storm and hyper-inflammation mediated by NLRP3 inflammasome activation and/or one or more symptoms associated with such cytokine storm and hyper-inflammation. In particular, the present disclosure relates to esters, (R)-3-hydroxybutyric acid, (R)-3-hydroxybutyric acid salt and oligomers of (R)-3-hydroxybutyric acid that are capable of elevating blood levels of (R)-3-hydroxybutyric acid to concentrations sufficient to have any of the effects described above.

BACKGROUND

Covid-19 is a viral infection caused by severe acute respiratory syndrome coronavirus 2 (SARS-CoV-2). The most common symptoms of Covid-19 are fever, cough, headaches, fatigue, muscle or body aches, loss of taste or smell, sore throat, nausea, and diarrhea. The signs of serious illness include trouble breathing, persistent pain or pressure in the chest, new confusion, inability to wake or stay awake, and pale, gray, or blue colored skin, lips, or nail beds (depending on skin tone). Symptoms can begin one to fourteen days after exposure to the virus. Of those people who develop noticeable symptoms, 81% develop mild to moderate symptoms, while 14% develop severe symptoms, and 5% suffer critical symptoms (respiratory failure, shock, or multi-organ dysfunction). At least a third of the people who are infected with the virus remain asymptomatic and do not develop noticeable symptoms at any point in time. Some people continue to experience a range of effects—known as long CoVID—for weeks to months after recovery.

The development of effective molecules that can treat, reduce, ameliorate, or block the cytokine storm and hyper-inflammation mediated by NLRP3 inflammasome activation and/or one or more symptoms associated with such cytokine storm and hyper-inflammation could mean the difference between life or death.

SUMMARY

The present disclosure relates to ketogenic compounds and compositions comprising ketogenic compounds, capable of reducing adverse effects caused by or associated with a viral infection, such as the adverse effects caused by or associated with Covid-19 infection caused by the SARS-CoV-2 virus. The present disclosure also provides methods of using such ketogenic compounds and compositions comprising such ketogenic compounds to treat, reduce, ameliorate, or block one the cytokine storm and hyper-inflammation mediated by NLRP3 inflammasome activation and/or one or more symptoms associated with such cytokine storm and hyper-inflammation. In particular, the present disclosure relates to (R)-3-hydroxybutyric acid and esters, salts, and oligomers thereof that are capable of elevating blood levels of (R)-3-hydroxybutyric acid to concentrations sufficient to have any of the effects described above.

In some embodiments, the present disclosure is directed to a method of treating the symptoms of a viral infection caused by SARS-CoV-2, in a subject in need of thereof, comprising administering to the subject suffering the from the symptoms of the viral infection, a therapeutically effective amount of a compound according to Formula I

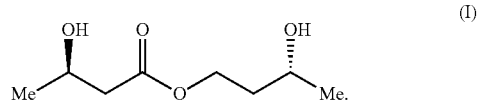 [SMILES: C[C@@H](O)CCOC(=O)C[C@@H](C)O]

In some embodiments, the compound of Formula I is administered as a constituent of a ketogenic composition comprising the compound of Formula I and a pharmaceutically acceptable carrier.

In some embodiments, the method further comprises administering one or more additional ketogenic compounds.

In some embodiments, the administration is oral or intravenous administration.

In some embodiments, administering the compound according to Formula I results in a blood ketone body concentration from about 0.1 mM to about 20 mM.

In some embodiments, the blood ketone body concentration is about 1 mM to about 5 mM.

In some embodiments, the compound according to Formula I is administered in a dose of about 5 g to about 500 g.

In some embodiments, the compound according to Formula I is administered in a dose of 51 g to about 75 g.

In some embodiments, the compound according to Formula I is administered in a dose of about 0.08 g to about 8 g per kilogram of the subject's body weight.

In some embodiments, the compound according to Formula I is administered to the subject in need thereof in a dose of 0.8 g/kg to about 1.5 g/kg based on the subject's body weight.

In some embodiments, the method further comprises administering vitamin C.

In some embodiments, the vitamin C is administered in a dose of about 1 g to about 100 g.

In some embodiments, the method further comprises administering at least one of a 3-hydroxybutyric acid salt, 1,3-butanediol, ethyl hydroxybutyrate, or MCT oil.

In some embodiments, the 3-hydroxybutyric acid salt is selected from the group consisting of sodium 3-hydroxybutanoate, magnesium 3-hydroxybutanoate, calcium 3-hydroxybutanoate, potassium 3-hydroxybutanoate, and combinations thereof.

In some embodiments, the MCT oil is a MCT (C8) oil.

In some embodiments, the method further comprises administering nicotinamide riboside and a methyl donor.

In some embodiments, the symptoms of Covid-19 are long-term symptoms.

In some embodiments, the long-term symptoms are selected from the group consisting of fatigue, shortness of breath, cough, joint pain, chest pain, difficulty with thinking and concentration (brain fog), depression, muscle pain, headache, intermittent fever, fast-beating or pounding heart, heart palpitations, inflammation of the heart muscle, lung function abnormalities, acute kidney injury, rash, hair loss, smell and taste problems, sleep issues, difficulty with concentration, memory problems, anxiety, change of mood, and combinations thereof.

In some embodiments, the method further comprises administering one or more of the following: a 3-hydroxybutyric acid salt; 1,3-butanediol; MCT C8 oil; or 3-hydroxybutyric acid. In some embodiments, the 3-hydroxybutyric acid salt is selected from the group consisting of sodium 3-hydroxybutanoate, magnesium 3-hydroxybutanoate, calcium 3-hydroxybutanoate, potassium 3-hydroxybutanoate, and combinations thereof.

In some embodiments, the compound of Formula I is enantiomerically enriched to about 90%.

In some embodiments, the compound of Formula I is enantiomerically enriched to about 99.99%.

In some embodiments, the method further comprises administering (3S)-hydroxybutyl (3S)-hydroxybutanoate and wherein the (3S)-hydroxybutyl (3S)-hydroxybutanoate and the compound of Formula I are present in a ratio of 1:1.

In some embodiments, the present disclosure is directed to a method of alleviating the symptoms associated with a cytokine storm and hyper-inflammation, in a subject in need of thereof, comprising administering to the subject a therapeutically effective amount of a compound according to Formula I

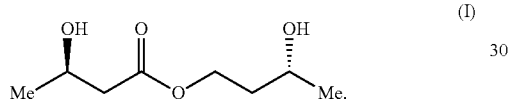

(I)

monoester (R)-3-hydroxybutyl (R)-3-hydroxybutanoate, a ketone body salt or mixture of ketone body salts (e.g. sodium, magnesium, calcium and potassium salts), and combinations thereof. As used herein, ketone ester refers to a compound that contains one or more ester groups. Examples of ketone esters with more than one ester group are butane-1,3-diyl bis(3-hydroxybutanoate) and 3-((3-((3-hydroxybutanoyl)oxy)butanoyl)oxy)butanoic acid, both of which are shown below.

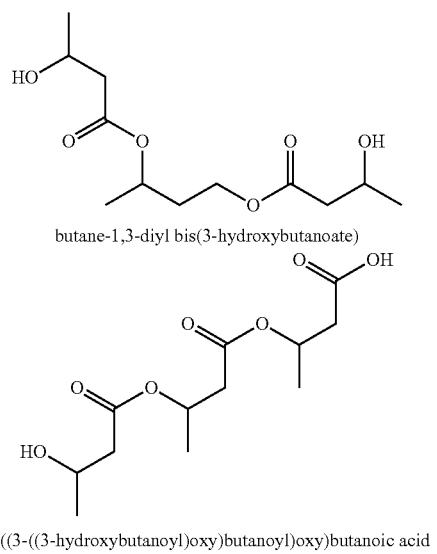

butane-1,3-diyl bis(3-hydroxybutanoate)

3-((3-((3-hydroxybutanoyl)oxy)butanoyl)oxy)butanoic acid

DETAILED DESCRIPTION

It has been surprisingly discovered that protection against the cytokine storm, caused or associated with SARS-CoV-2 viral infection (Covid-19), can be increased by increasing the concentration of ketone bodies or the concentration of a ketogenic compound in the blood. The ketone body and/or ketogenic compound can be administered through any permissible route of administration, including through oral or intravenous (IV) delivery. In certain embodiments, the ketone body can be a ketone monoester, a ketone body precursor, a ketone body analog, or combination thereof. In certain embodiments, the ketone body can be administered alone or in combination with one or more ketone body salts.

As used herein, a ketone body salt is a salt of a compound that contains both a ketone group and a carboxylic acid group.

As used herein, ketone monoester is a compound that contains an ester group. An example of a ketone monoester is (R)-3-hydroxybutyl (R)-3-hydroxybutanoate.

As used herein, ketone body precursor or ketone body analog is a compound that is metabolized or converted to 3-hydroxybutyric acid. Examples of a ketone body precursor or ketone body analog are Medium-chain Triglycerides (MCT-oil) and 1,3-butanediol.

Such ketogenic compounds can interrupt the body's erroneous overreaction to fighting the SARS-CoV-2 virus which places the subject in a rapidly deteriorating position that can frequently result in the subject's death.

In some embodiments, a ketogenic composition can comprise one or more ketone bodies. In some embodiments, the ketone body can be selected from the group consisting of 3-hydroxybutyric acid, a ketone ester, such as ketone In some embodiments, 3-hydroxybutyric acid can be substantially pure (R)-3-hydroxybutyric acid or substantially pure (S)-3-hydroxybutyric acid, or a combination thereof. Exemplary mixtures can comprise, for example, about 80%, about 85%, about 90%, about 95%, about 96%, about 97%, about 98%, about 99%, about 99.9%, or about 99.99% (R)-3-hydroxybutyric acid, with the remainder comprising the other enantiomer. In other embodiments, the mixture can comprise about 80%, about 85%, about 90%, about 95%, about 96%, about 97%, about 98%, or about 99% (S)-3-hydroxybutyric acid, with the remainder being the other enantiomer. In some embodiments, the percentage of (R)-3-hydroxybutyric acid in the mixture can be about 5%, about 10%, about 15%, about 20%, about 25%, about 30%, about 35%, about 40%, about 45%, about 50% (a racemic mixture), about 55%, about 60%, about 65%, about 70%, 7 about 5%, about 80%, about 85%, about 90%, or about 95%.

In some embodiments, and unless otherwise noted, a reference to 3-hydroxybutyric acid, will be understood to encompass either enantiomer free of the other enantiomer, as well as any mixture of (R)-3-hydroxybutyric acid and (S)-3-hydroxybutyric acid.

In some embodiments, the ketone body can be in the form of an enantiomerically enriched compound as described in WO 2010/021766 (which is hereby incorporated by reference in its entirety), such as 3-hydroxybutyl 3-hydroxybutanoate being enantiomerically enriched with respect to the (3R, 3R') enantiomer. In some embodiments, the 3-hydroxybutyl 3-hydroxybutyrate can be enantiomerically enriched to about 90%, about 95%, about 96%, about 97%, about 98%, about 99%, about 99.9%, or about 99.99% of the (3R)-hydroxybutyl (3R)-hydroxybutanoate enantiomer. In some embodiments, the 3-hydroxybutyl 3-hydroxybutyrate can be 3-hydroxybutyl (3R)-hydroxybutanoate.

In some embodiments, the ketone ester can be an ester of 3-hydroxybutyric acid. In some embodiments, the ketone ester can be selected from the group consisting of the methyl, ethyl, propyl (e.g. n-propyl or 2-propyl), butyl (e.g. tert-butyl), pentyl, hydroxybutyl (e.g. 3-hydroxybutyl), hydroxypropyl, glyceryl (e.g. 2,3-dihydroxypropyl) ester of 3-hydroxybutyric acid, and combinations thereof. In vivo, these ketone esters are de-esterified by esterase enzymes, releasing 3-hydroxybutyric acid. Such ketone esters can have improved solubility, increased membrane permeability, improved stability, and/or more sustained release compared to native 3-hydroxybutyric acid.

In some embodiments, the ketogenic compound can be a salt of 3-hydroxybutyric acid or a mixture of 3-hydroxybutyric acid salts. Exemplary 3-hydroxybutyric acid salts include, but are not limited to, sodium, magnesium, calcium, and potassium 3-hydroxybutanoate, and combinations thereof.

In some embodiments, this disclosure provides ketogenic compositions comprising one or more ketogenic compounds. Exemplary compositions can comprise one or more ketogenic compounds and a pharmaceutically acceptable carrier. The term "pharmaceutically acceptable carrier" encompasses any of the standard pharmaceutical carriers, solvents, surfactants, or vehicles. Suitable pharmaceutically acceptable vehicles include aqueous vehicles and nonaqueous vehicles. Standard pharmaceutical carriers and their formulations are described in Remington's Pharmaceutical Sciences, Mack Publishing Co., Easton, PA, 19th ed. 1995. In some embodiments the pharmaceutically acceptable carrier can be water, saline (including isotonic saline), 1,3-butanediol, or combinations thereof. In some embodiments, the ketogenic composition can be sweetened or otherwise flavored to mask any undesirable tastes associated with the ketogenic compound or compounds present in the composition.

In some embodiments, the ketogenic composition can comprise 1,3-butanediol. 1,3-butanediol is water soluble and well tolerated by animals, including humans. In the body, it is efficiently converted to 3-hydroxybutyric acid by enzymatic and/or chemical action such as when an alcohol dehydrogenase catalyzes the metabolism of 1,3-butanediol to 3-hydroxybutyraldehyde, which is subsequently oxidized to 3-hydroxybutyrate by aldehyde dehydrogenase. Advantageously, 1,3-butanediol is neutral and can be administered directly without the need to formulate as a salt. In some embodiments, 1,3-butanediol can be substantially pure (R)-1,3-butanediol or substantially pure (S)-1,3-butanediol, or a combination thereof. Exemplary mixtures can comprise, for example, about 80%, about 85%, about 90%, about 95%, about 96%, about 97%, about 98%, about 99%, about 99.9%, or about 99.99% (R)-1,3-butanediol, with the remainder comprising the other enantiomer. In other embodiments, the mixture can comprise about 80%, about 85%, about 90%, about 95%, about 96%, about 97%, about 98%, about 99%, about 99.9%, or about 99.99% (S)-1,3-butanediol, with the remainder being the other enantiomer. In some embodiments, 1,3-butanediol is racemic.

In some embodiments, the ketogenic composition can comprise a fat molecule capable of being readily converted to ketogenic compounds in the body. In some embodiments, the ketogenic composition can comprise a medium chain triglyceride (MCT), for example, a triglyceride comprising carbon chains with 6 to 12 carbon (e.g. MCT C8 oil). MCTs are more efficiently converted to ketones in vivo than shorter or longer chain fats. Exemplary MCTs include, but are not limited to, caproic acid (C6), caprylic acid (C8), capric acid (C10), and lauric acid (C12).

In some embodiments, the ketogenic composition can further comprise a nicotinamide adenine dinucleotide modulator (e.g. nicotinamide riboside) and a methyl donor as described in U.S. Pat. No. 10,376,528 (which is incorporated by reference in its entirety). In some embodiments, the nicotinamide riboside and a methyl donor are administered sequentially or simultaneously with the administration of the ketogenic compound or ketogenic composition.

In some embodiments, the ketogenic compound or ketogenic composition can be administered to treat a viral infection or alleviate the symptoms caused by SARS-CoV-2 resulting in cytokine storms and the resulting disease (Covid-19), where the composition comprises one or more ketone bodies and a pharmaceutically acceptable carrier.

In some embodiments, the ketogenic composition can be administered to treat a viral infection or alleviate the symptoms caused by SARS-CoV-2 resulting in cytokine storms and the resulting disease (Covid-19), wherein the composition can comprise a ketone ester, such as 3-hydroxybutyl 3-hydroxybutanoate.

In some embodiments, the ketogenic composition can be administered treat a viral infection or alleviate the symptoms caused by SARS-CoV-2 resulting in cytokine storms and the resulting disease (Covid-19), where the composition comprises a ketone ester, such as (R)-3-hydroxybutyl (R)-3-hydroxybutanoate.

In some embodiments, the present disclosure provides a method of treating a subject that is suspected of having Covid-19 comprising administering to that subject a therapeutically effective amount of a ketogenic composition comprising a ketone body. In some embodiments, the ketone body can be a ketone ester. In some embodiments, the ketone ester is (R)-3-hydroxybutyl (R)-3-hydroxybutanoate taught by WO2010/120300 and WO2010/021766 (which are both incorporated by reference in their entirety)

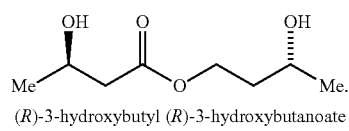

(R)-3-hydroxybutyl (R)-3-hydroxybutanoate (I)

In some embodiments, the method comprises treating a viral infection, or alleviating the symptoms of a viral infection, in a subject in need thereof comprising administering to the subject a therapeutically effective amount of a ketogenic composition. The viral infection may be an infection caused by any pathogenic virus, for example influenza viruses, coronaviruses such as SARS-CoV-2, HIV, noroviruses, respiratory syncytial viruses, herpes viruses, and papillomaviruses. In some embodiments, the viral infection is caused by coronavirus and any relevant variants including but not limited to variants of SARS-CoV-2. In some embodiments, the viral infection is caused by SARS-CoV-2 and any relevant variants including but not limited to SARS-CoV-2 varients VOC-20DEC-01, VOC-20DEC-02, VOC-21JAN-02, VUI-21FEB-03, 501Y-V2, 19A, 19b, 20A, 20A.EU1, 20AEU2, 20B, 20B/501.V1 (B.1.1.7), 20C. B.1.1.201, B.1.429, B.1.427, B.1.351, P.1, P.2, B.1.526, B.1.525, and B.1.135. As used herein "Covid-19" refers to the viral infection caused by SARS-CoV-2 and any relevant variants thereof.

In some embodiments, the method comprises alleviating the symptoms of a viral infection in a subject in need thereof, the method comprising administering to the subject a therapeutically effective amount of a ketogenic composition. In some embodiments, the method comprises alleviating the symptoms associated with the cytokine storm and hyper-inflammation mediated by NLRP3 inflammasome activation and/or one or more symptoms associated with such cytokine storm and hyper-inflammation. In some embodiments, the symptom associated with such cytokine storm and hyper-inflammation includes but not limited to breathing impairment.

There are many ways CoVID-19 can affect the health of a subject. Most subjects with CoVID-19 recover and return to normal health, however, some subjects can have symptoms that can last for weeks or even months after recovery from acute illness. Even subjects who are not hospitalized and who have mild illness, at least initially, can experience persistent, late or long-term symptoms.

In some embodiments, the present disclosure provides a method of alleviating the symptoms of a viral infection where the symptoms are long-term symptoms. In some embodiments, the viral infection can be a SARS-CoV-2 viral infection. In certain embodiments, the symptoms that can be alleviated are the long term symptoms associated with "long Covid." As used herein "long Covid" refers to the persistent symptoms that a person testing positive for Covid-19 can display after recovering and returning to normal health. These symptoms can last for weeks or months after recovery from acute illness. In some embodiments, the symptoms and/or long-term symptoms associated with long Covid include, but are not limited to, fatigue, shortness of breath, cough, joint pain, chest pain, difficulty with thinking and concentration (brain fog), depression, muscle pain, headache, intermittent fever, fast-beating or pounding heart, heart palpitations, inflammation of the heart muscle, lung function abnormalities, acute kidney injury, rash, hair loss, smell and taste problems including the loss of one or both of taste or smell, sleep issues including insomnia, difficulty with concentration, memory problems, anxiety, change of mood, and combinations thereof.

In some embodiments, the present disclosure provides a ketogenic composition comprising a ketone ester and/or a mixture of ketogenic compounds, along with vitamin C. Without wishing to be bound by a particular theory, it is believed that combining vitamin C with any of the ketone bodies or ketogenic compounds described herein can dramatically increase the antioxidant properties of vitamin C. In some embodiments, the vitamin C is administered sequentially or simultaneously with the administration of the ketogenic compound or ketogenic composition. In some embodiments, a ketogenic composition comprising vitamin C can comprise between about 1 g to about 100 g, about 5 g to about 20 g, or about 10 g to about 15 g of vitamin C. The composition can be administered to a subject in need thereof in escalating amounts until the body reaches a state of tolerance.

In some embodiments, treatment can achieved by administering the ketone body, ketogenic compound, or ketogenic composition by oral, intravenous, or parenteral administration in an amount sufficient to raise the blood ketone body concentration to between about 0.1 mM to about 20 mM, about 0.2 mM to about 10 mM, about 2 mM to about 8 mM, about 0.8 mM to about 4.0 nM, or about 1 mM to about 5 mM.

In some embodiments, the dose of the one or more ketogenic compounds can be between about 5 g to about 500 g, about 10 g to about 450 g, about 20 g to about 400 g, about 30 g to about 350 g, about 40 g to about 300 g, about 50 g to about 250 g, about 130 g to about 170 g, 51 g to about 200 g, 51 g to about 150 g, 51 g to about 100 g, or 51 g to about 75 g of a ketone body or mixtures of ketone bodies. In some embodiments, the dose can be between about 0.08 g/kg to about 8 g/kg, about 0.1 g/kg to about 5 g/kg, about 0.5 g/kg to about 2 g/kg, about 0.8 to about 4 g/kg, about 0.8 g/kg to about 3 g/kg, about 0.8 g/kg to about 2 g/kg, about 0.8 g/kg to about 1.5 g/kg, about 0.56 g/kg to about 0.83 g/kg, about 0.56 g/kg to about 1.7 g/kg, about 0.56 g/kg to about 2.2 g/kg, about 0.66 g/kg to about 0.96 g/kg, about 0.66 g/kg to about 1.9 g/kg, about 0.66 g/kg to about 2.6 g/kg, to about 0.82 g/kg to about 1.2 g/kg, about 0.82 g/kg to about 2.4 g/kg, or about 0.82 g/kg to about 3.2 g/kg, based on the subject's body weight.

In some embodiments, the method of treating the viral disease, such as Covid-19, or alleviating the symptoms of a viral infection, comprises administering an effective amount of the ketogenic composition before, during or after exposure to the infectious virus, i.e. SARS-CoV-2, to the subject. In some embodiments, the method of treating the viral disease comprises administering an effective amount of the ketogenic composition as a prophylactic. In some embodiments, the method of treating the viral disease comprises administering an effective amount of the ketogenic composition two weeks prior to potential exposure to SARS-Cov-2, after testing positive for the virus and being diagnosed with Covid-19, and/or within two weeks following testing positive for Covid-19. In some embodiments, the method of treating the viral disease comprises administering an effective amount of the ketogenic composition prior to being vaccinated for SARS-CoV-2 and/or any relevant variant. In some embodiments, the method of treating the viral disease comprises administering an effective amount of the ketogenic composition prior to and after being vaccinated for SARS-CoV-2 and/or any relevant variant.

In some embodiments, the method comprises alleviating the symptoms associated with the cytokine storm and hyper-inflammation, in a subject in need thereof comprising administering to the subject a therapeutically effective amount of a ketogenic composition during or after the onset of the cytokine storm and hyper-inflammation. In some embodiments, the method of alleviating the symptoms associated with the cytokine storm and hyper-inflammation comprises administering an effective amount of the ketogenic composition as a prophylactic.

In some embodiments, the method treating the viral disease, such as Covid-19, or alleviating the symptoms of a viral infection, comprises administering an effective amount of the ketogenic composition on an empty stomach, while on a low-glycemic diet, low-carbohydrate diet, or low-glucose diet, or combinations thereof.

In some embodiments, the method comprises alleviating the symptoms associated with the cytokine storm and hyper-inflammation, comprises administering an effective amount of the ketogenic composition on an empty stomach, while on a low-glycemic diet, low-carbohydrate diet, or low-glucose diet, or combinations thereof.

In some embodiments, the method of treating the viral disease in a subject in need thereof comprises administering an effective amount of the ketogenic composition after a subject is already at the stage of severe life threatening state after being exposed to SARS-CoV-2.

EXPERIMENTAL

Example 1

A female test subject was diagnosed with Covid-19 in the hospital. While in the hospital, the subject received steroids due to troubled breathing after which the hospital discharged the subject. After being at home for several days the subject began having labored breathing and chills but did not have a fever. The test subject decided to drink 1 bottle of KetoneAid® KE1 (on an empty stomach). KetoneAid® KE1 contains a total of 5.0 g of ketone bodies (specifically: 2.5 g of (R)-ketone ester and 2.5 g of (R)-3-hydroxybutyric acid and (R)-3-hydroxybutyric acid salts (including sodium (135 mg), potassium (135 mg), magnesium (59 mg) and calcium (39 mg) salts). After approximately 8 minutes, test subject reported less labored breathing and an overall improvement in breathing. In addition, the test subject no longer had the chills. The test subject continued to drink 1 bottle of KetoneAid® KE1 on an empty stomach twice a day such that the subject received a total dose of 10 g of ketone bodies daily.

Example 2

A male test subject diagnosed with Covid-19 resting at home was admitted to the hospital after his condition deteriorated significantly. At the hospital, he was administered oxygen and scheduled for a ventilator. Prior to being placed on a ventilator, the subject received 10 g of active ketone ester (20 mL of KetoneAid® KE4 containing (R)-3-hydroxybutyl-(R)-3-hydroxybutanoate). After 3 hours, the subject no longer needed supplemental oxygen. The subject continued to receive 20 mL of KetoneAid® KE4 in the morning on an empty stomach for 3 days. The subject was discharged from the hospital 3 days after receiving the active ketone ester.

Example 3

Four male test subjects diagnosed with Covid-19 were tested for lung capacity by measuring their Forced Vital Capacity (FVC), Forced Expiratory Volume (FEV1) and for two of the subjects their Partial Pressure of Oxygen (pO2). Their lung capacity was measured before, 15 min after, and 30 min after receiving 7.5 g of active ketone ester (15 mL of KetoneAid® KE4 containing (R)-3-hydroxybutyl-(R)-3-hydroxybutanoate). Three of the subjects received active ketone ester on an empty stomach and one subject received active ketone ester with food. All of the subjects receiving the ketone ester on an empty stomach showed improved lung capacity. The subject that received ketone ester with food did not show significant improved lung capacity. Results from this study are shown in Table 1

TABLE 1

Before and after consuming 7.5 g of Active Ketone Ester (15 ml KE4) on Covid Positive Patients Apr. 23, 2020

|  |  |  |  | Before Ketones | | 15 Min | | 30 Min | | RESULTS |
| --- | --- | --- | --- | --- | --- | --- | --- | --- | --- | --- |
| Patient 1 | Sex | Age | Weight | FVC | FVC % | FVC | FVC % | FVC | FVC % | Total Air |
| Empty Stomach | M | 60 | 98k | 4.64 | 107% | 5.33 | 123% | 5.46 | 126% | 17.7% Increase |
|  |  |  |  | FEV1 Sec | FEV1% | FEV1 Sec | FEV1% | FEV1 Sec | FEV1% | 1 Second Breath |
|  |  |  |  | 3.98 | 116% | 4.32 | 126% | 4.78 | % | 20% Increase |
| Patient 2 | Sex | Age | Weight | FVC | FVC % | FVC | FVC % | FVC | FVC % | Total Air |
| Empty Stomach | M | 54 | 57k | 4.18 | 90% | 4.88 | 105% | 5.04 | 109% | 20.6% Increase |
|  |  |  |  | FEV1 Sec | FEV1% | FEV1 Sec | FEV1% | FEV1 Sec | FEV1% | 1 Second Breath |
|  |  |  |  | 3.47 | 93% | 3.5 | 94% | 3.48 | 94% | No Change |
| Patient 3 | Sex | Agg | Weight | FVC | FVC % | FVC | FVC % | FVC | FVC % | Total Air |
| WITH FOOD | M | 45 | 87.5k | 4.27 | 109% | 4.26 | 108% | 4.24 | 108% | No Change |
| (didn't work) |  |  |  | FEV1 Sec | FEV1% | FEV1 Sec | FEV1% | FEV1 Sec | FFV1% | 1 Second Breath |
|  |  |  |  | 3.25 | 110% | 3.56 | 109% | 3.62 | 111% | 11% Incease |
|  |  |  |  | pO2 | Glucose | pO2 | Glucose | pO2 | Glucose | Blood Glucose |
|  |  |  |  | 97 | 140 | 97 | 129 | 97 | 100 | 28.5% Drop |
|  |  |  |  | feeling 70% |  | feeling 70% |  | feeling 70% |  |  |
| Patient 4 | Sex | Age | Weight | FVC | FVC % | FVC | FVC % | FVC | FVC % | Total Air |
| Empty Stomach | M | 55 | 113k | 2.84 | 62% | 5.09 | 110% | 4.27 | 93% | 50% Increase |
|  |  |  |  | FEV1 Sec |  | FEV1 sec | FEV1% | FEV1 Sec | FEV1% | 1 Second Breath |
|  |  |  |  | 1.87 | 51% | 4.11 | 111% | 3.39 | 92% | 81% Increase |
|  |  |  |  | pO2 | Glucose | pO2 | Glucose | pO2 | Glucose | Blood Glucose |
|  |  |  |  | 96 | 144 | 96 | 126 | 97 | 108 | 25% Drop |
|  |  |  |  | feeling 65% |  | feeling 75% |  | feeling 75% |  | Feeling after ride home 85% |

FVC = Forced Vital Capacity (total air in 1 breathe)
FEV1 = Forced Expiratory Volume (1st second of breathe)
pO2 = Partial Pressure of Oxygen

I claim:

1. A method of treating the symptoms of a viral infection caused by SARS-CoV-2 in a subject in need of thereof, comprising administering to the subject suffering from the symptoms of the viral infection, a therapeutically effective amount of the compound according to Formula I, or a composition comprising a therapeutically effective amount of the compound of Formula I

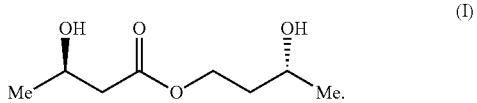 [SMILES: C[C@@H](O)CCOC(=O)C[C@@H](C)O]
(I)

2. The method of claim 1, wherein the compound of Formula I is administered as a composition comprising the compound of Formula I and a pharmaceutically acceptable carrier.

3. The method of claim 1, wherein the administration is oral or intravenous administration.

4. The method of claim 3, wherein administering the compound according to Formula I results in a blood ketone body concentration from about 0.1 mM to about 20 mM.

5. The method of claim 3, wherein the blood ketone body concentration is about 1 mM to about 5 mM.

6. The method of claim 3, wherein the compound according to Formula I is administered in a dose of about 0.08 g to about 8 g per kilogram of the subject's body weight.

7. The method of claim 4, wherein the compound according to Formula I is administered to the subject in need thereof in a dose of 0.8 g/kg to about 1.5 g/kg based on the subject's body weight.

8. The method of claim 1, wherein the method further comprises administering vitamin C where in the vitamin C is administered in a dose of about 1 g to about 100 g.

9. The method of claim 1, wherein the method further comprises administering at least one of a 3-hydroxybutyric acid salt, 1,3-butanediol, ethyl hydroxybutyrate, or MCT oil.

10. The method of claim 9, wherein the 3-hydroxybutyric acid salt is selected from the group consisting of sodium 3-hydroxybutanoate, magnesium 3-hydroxybutanoate, calcium 3-hydroxybutanoate, potassium 3-hydroxybutanoate, and combinations thereof.

11. The method of claim 9, wherein the MCT oil is a MCT (C8) oil.

12. The method of claim 1, wherein the method further comprises administering nicotinamide riboside.

13. The method of claim 1, wherein the symptoms of Covid-19 are long-term symptoms.

14. The method of claim 13, wherein the long-term symptoms are selected from the group consisting of fatigue, shortness of breath, cough, joint pain, chest pain, difficulty with thinking and concentration (brain fog), depression, muscle pain, headache, intermittent fever, fast-beating or pounding heart, heart palpitations, inflammation of the heart muscle, lung function abnormalities, acute kidney injury, rash, hair loss, smell and taste problems, sleep issues, difficulty with concentration, memory problems, anxiety, change of mood, and combinations thereof.

15. The method of claim 1, wherein the method further comprises administering one or more of the following:
   a) a 3-hydroxybutyric acid salt;
   b) 1,3-butanediol;
   c) MCT C8 oil; or
   d) 3-hydroxybutyric acid; and
wherein the 3-hydroxybutyric acid salt is selected from the group consisting of sodium 3-hydroxybutanoate, magnesium 3-hydroxybutanoate, calcium 3-hydroxybutanoate, potassium 3-hydroxybutanoate, and combinations thereof.

16. The method of claim 1, wherein the compound of Formula I is enantiomerically enriched to about 90%.

17. The method of claim 1, wherein the compound of Formula I is enantiomerically enriched to about 99.99%.

18. The method of claim 1, wherein the method further comprises administering (3S)-hydroxybutyl (3S)-hydroxybutanoate and wherein the (3S)-hydroxybutyl (3S)-hydroxybutanoate and the compound of Formula I are present in a ratio of 1:1.

19. A method of alleviating the symptoms associated with a cytokine storm and hyper-inflammation, in a SARS-CoV-2 subject in need of thereof, comprising administering to the subject a therapeutically effective amount of the compound according to Formula I

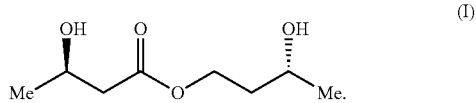 [SMILES: C[C@@H](O)CCOC(=O)C[C@@H](C)O]
(I)

* * * * *